United States Patent [19]

Sato et al.

[11] Patent Number: 5,627,251
[45] Date of Patent: May 6, 1997

[54] ORGANOSILICON COMPOUND AND PROCESS FOR ITS PRODUCTION

[75] Inventors: Shinichi Sato; Noriyuki Koike; Takashi Matsuda; Kouichi Ishida, all of Matsuida, Japan

[73] Assignee: Shin-Etsu Chemical Co., Ltd., Tokyo, Japan

[21] Appl. No.: 491,110

[22] Filed: Jun. 16, 1995

[30] Foreign Application Priority Data

Jun. 17, 1994 [JP] Japan .................. 6-159510

[51] Int. Cl.$^6$ .................................. C08G 77/08
[52] U.S. Cl. ................... 528/15; 528/26; 528/31; 528/42; 556/419
[58] Field of Search .................. 528/26, 42, 31, 528/15; 556/419

[56] References Cited

U.S. PATENT DOCUMENTS

| | | | |
|---|---|---|---|
| 3,828,087 | 8/1974 | Pittman et al. | 528/42 |
| 5,120,810 | 6/1992 | Fiyiki et al. | 528/15 |
| 5,314,981 | 5/1994 | Takago et al. | 528/36 |
| 5,326,611 | 7/1994 | Kishita et al. | 428/78 |

FOREIGN PATENT DOCUMENTS

| | | | |
|---|---|---|---|
| 0328397 | 8/1989 | European Pat. Off. | C07F 7/21 |
| 0538062A2 | 4/1993 | European Pat. Off. | C07F 7/21 |
| 2097406 | 3/1972 | France | C07F 7/21 |
| 3830572A1 | 3/1989 | Germany | C07F 7/08 |

OTHER PUBLICATIONS

Chemical Abstracts, vol. 74, No. 25, Abstract No. 141952b (Jun. 21, 1971).

*Primary Examiner*—Margaret W. Glass
*Attorney, Agent, or Firm*—Cushman Darby & Cushman IP Group Pillsbury Madison & Sutro LLP

[57] ABSTRACT

An organosilicon compound represented by the general formula:

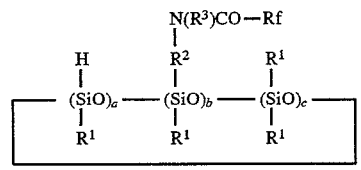

wherein Rf represents a perfluoroalkyl group or a perfluoroalkyl ether group; $R^1$ may be the same or different and each represent a monovalent hydrocarbon group; $R^2$ represents an alkylene group; $R^3$ represents a hydrogen atom or a monovalent hydrocarbon group; and a is an integer of 1 to 4, b is an integer of 1 to 3 and c is an integer of 0 to 3, provided that a, b and c satisfy the relationship of $3 \leq a+b+c \leq 6$; is provided. These organosilicon compounds are novel compounds useful as crosslinking agents for addition-curable silicone rubber compositions.

8 Claims, 7 Drawing Sheets

ORGANOSILICON COMPOUND AND PROCESS FOR ITS PRODUCTION

BACKGROUND OF THE INVENTION

1. Field of the Invention

This invention relates to a novel organosilicon compound useful as a crosslinking agent used in addition-curable silicone rubber compositions known to have various uses, and to a process for its production.

2. Description of the Prior Art

Curable silicone rubber compositions of addition reaction curing which are comprised of an organopolysiloxane having alkenyl groups such as vinyl groups, as a base polymer, and an organohydrogenpolysiloxane having SiH groups, incorporated in said base polymer as a crosslinking agent, are hitherto widely used for various purposes. The curable silicone rubber compositions of this type are cured by the addition reaction (hydrosilylation) of SiH groups of the crosslinking agent with alkenyl groups.

When, however, the base polymer is replaced with a fluorosilicone or fluoropolymer having a high fluorine content to effect curing by similar addition reaction (hydrosilylation), the crosslinking agent is not uniformly compatible with the base polymer fluorosilicone or fluorine polymer having a high fluorine content, if the conventionally known organohydrogenpolysiloxane having SiH groups is incorporated as the crosslinking agent. Thus, it has been difficult to obtain good cured products.

SUMMARY OF THE INVENTION

Accordingly, an object of the present invention is to provide a novel organosilicon compound which is readily compatible with a base polymer even when the fluorosilicone or fluoropolymer having a high fluorine content is used as the base polymer, and hence can realize a fluorine-rich addition-curable silicone rubber composition or addition-curable fluororubber composition; and a process for its production.

The present invention provides an organosilicon compound represented by the following general formula (1):

$$\begin{array}{c} R^3 \\ | \\ N-CO-Rf \\ H \quad R^2 \quad R^1 \\ | \quad | \quad | \\ \boxed{(SiO)_a - (SiO)_b - (SiO)_c} \\ | \quad | \quad | \\ R^1 \quad R^1 \quad R^1 \end{array} \quad (1)$$

wherein:

Rf represents a perfluoroalkyl group or a perfluoroalkyl ether group;

$R^1$ may be the same or different and each represent a monovalent hydrocarbon group;

$R^2$ represents an alkylene group;

$R^3$ represents a hydrogen atom or a monovalent hydrocarbon group; and a is an integer of 1 to 4, b is an integer of 1 to 3 and c is an integer of 0 to 3, provided that a, b and c satisfy the relationship of $3 \leq a+b+c \leq 6$.

The organosilicon compound of the present invention is a novel compound, and is especially useful as a crosslinking agent for addition-curable silicone rubber compositions. In particular, it is useful as a crosslinking agent for fluorine-rich addition-curable silicone rubber compositions or addition-curable fluororubber compositions.

DETAILED DESCRIPTION OF THE PREFERRED EMBODIMENTS

Figure 1:
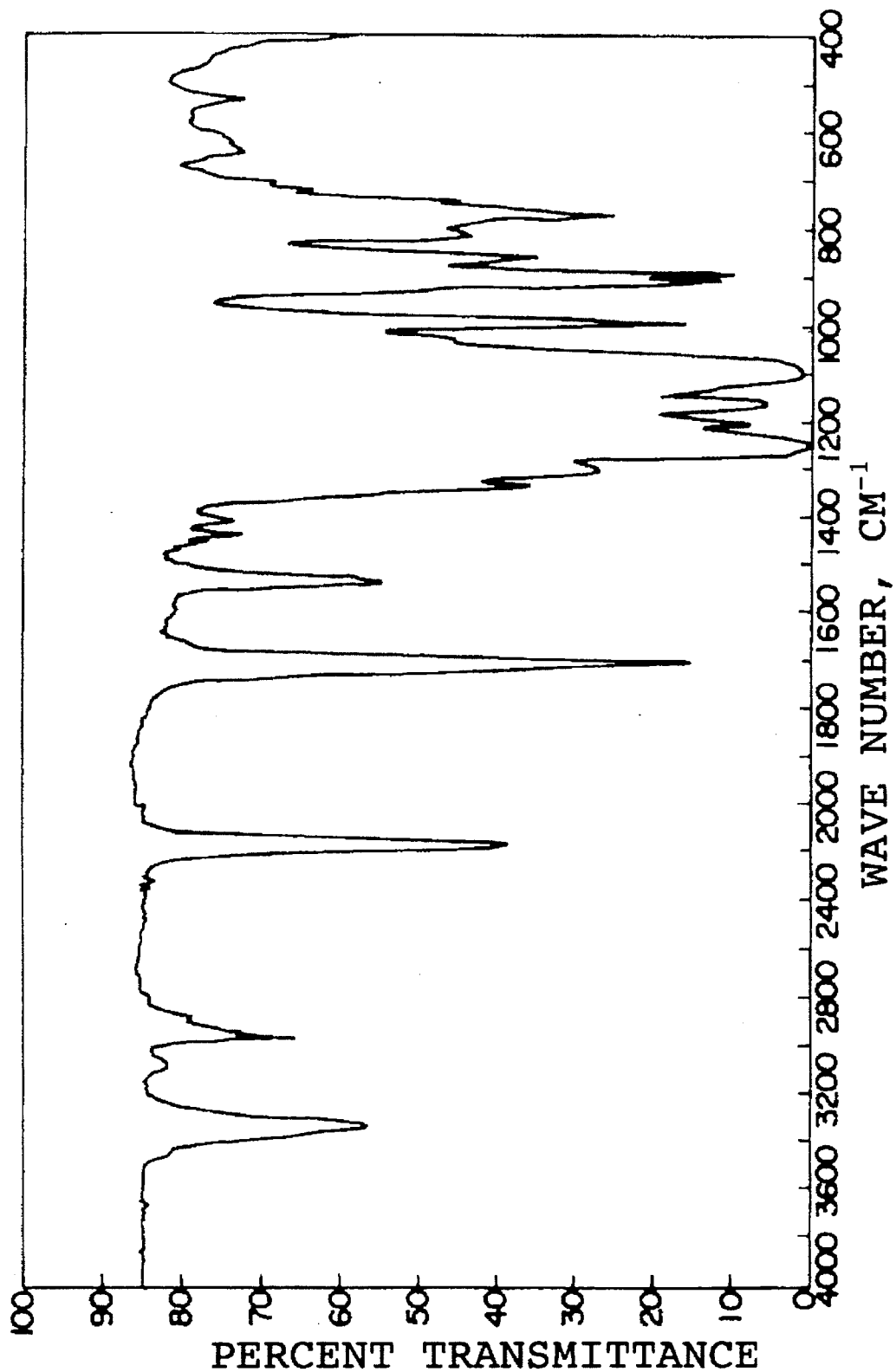
FIG. 1 is an IR chart of a compound synthesized in Example 1.

As is clear from the above general formula (1), the organosilicon compound of the present invention has SiH groups in its molecule. Hence, it can form a cured product by the hydrosilylation reaction of these groups with the unsaturated groups in unsaturated polymers. Namely, the organosilicon compound of the present invention can be used as a crosslinking agent in curable silicone rubber compositions of addition reaction curing.

In the above general formula (1), Rf is a perfluoroalkyl group or a perfluoroalkyl ether group. The perfluoroalkyl group may preferably be those having 1 to 10 carbon atoms, and the perfluoroalkyl ether group preferably those having 3 to 17 carbon atoms, more preferably 5 to 17 carbon atoms. The perfluoroalkyl group having 1 to 10 carbon atoms may include, for example, $-CF_3$, $-C_2F_5$, $-C_3F_7$, $-C_4F_9$, $-C_5F_{11}$, $-C_6F_{13}$, $-C_7F_{15}$, $C_8F_{17}$, $-C_{19}F_9$ and $-C_{10}F_{21}$. In particular, an especially preferred perfluoroalkyl group is $-CF_3$, $-C_4F_9$, $-C_6F_{13}$ and $-C_8F_{17}$. As for the perfluoroalkyl ether group having 3 to 17 carbon atoms may include, for example, the following.

a) $\begin{array}{c} -CF-(OCF_2CF)_n-F \\ | \quad\quad\quad | \\ CF_3 \quad\quad CF_3 \end{array}$ (wherein n is an integer of 1 to 5) such as, for example:

$\begin{array}{cc} -CFOCF_2CFOC_3F_7, & -CFOC_3F_7, \\ | \quad\quad | & | \\ CF_3 \quad CF_3 & CF_3 \end{array}$ $\begin{array}{c} -CFOCF_2CFOCF_2CFOC_3F_7, \quad \text{and} \\ | \quad\quad | \quad\quad | \\ CF_3 \quad\quad CF_3 \quad\quad CF_3 \end{array}$ $\begin{array}{c} -CFOCF_2CFOCF_2CFOCF_2CFOC_3F_7 \\ | \quad\quad | \quad\quad | \quad\quad | \\ CF_3 \quad CF_3 \quad CF_3 \quad CF_3 \end{array}$ b) $-CF_2-(OCF_2CF_2)_m-F$ (wherein m is an integer of 1 to 10)

c) $-CF_2CF_2O-(OCF_2CF_2CF_2)_m-F$ (wherein m is as defined above),

In particular, especially preferred perfluoroalkyl ether groups are the foregoing a).

$R^1$ is a monovalent hydrocarbon group, preferably including those having 1 to 10 carbon atoms, and in particular those having 1 to 8 carbon atoms, as exemplified by an alkyl group having 1 to 8 carbon atoms such as a methyl group, an ethyl group, a propyl group, an isopropyl group, a butyl group, a hexyl group, a cyclohexyl group or an octyl group; an alkenyl group having 2 to 8 carbon atoms such as a vinyl group, an allyl group, a propenyl group, an isopropenyl group, a butynyl group or a hexenyl group; a cycloalkenyl group having 6 to 10 carbon atoms such as cyclohexenyl group, or a cycloheptynyl group; an aryl group having 6 to 10 carbon atoms such as a phenyl group, a tolyl group, a xylyl group or a naphthyl group; and an aralkyl group having 7 to 10 carbon atoms such as a benzyl group or a phenylethyl group. In particular, those containing no aliphatic unsaturated bonds are preferred. For the use in crosslinking agents, $R^1$ may usually be preferably an alkyl group having 1 to 6 carbon atoms, and most preferably a methyl group.

$R^2$ is an alkylene group such as methylene, ethylene, methylethylene, tetramethylene or hexamethylene, and preferably those having 1 to 6 carbon atoms, particularly preferably those having 2 to 4 carbon atoms, and most preferably a trimethylene group.

$R^3$ is a hydrogen atom or a monovalent hydrocarbon group. Usually the monovalent hydrocarbon group typically includes those having 1 to 8 carbon atoms, in particular, those having 1 to 6 carbon atoms, specifically including those exemplified for $R^1$. $R^3$ is preferably a hydrogen atom, an alkyl group having 1 to 6 carbon atoms or a phenyl group, and more preferably a hydrogen atom, a methyl group, an ethyl group, a propyl group, an isopropyl group or a phenyl group.

As typical examples of the above organosilicon compound of the present invention, the compound can be exemplified by, but is not limited to, the following. In the present specification, Me represents a methyl group, and Ph a phenyl group.

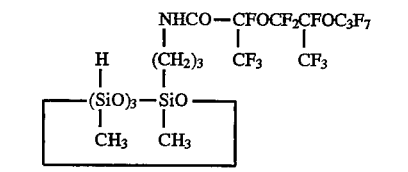

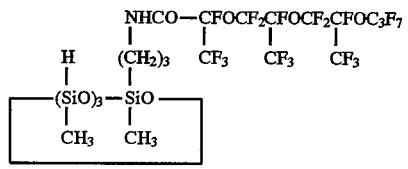

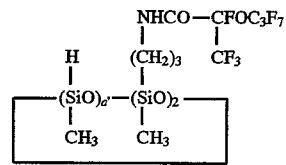

(wherein a' is 2 or 3)

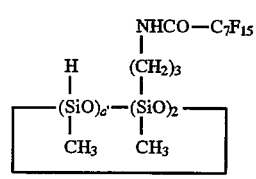

(wherein a' is 2 or 3)

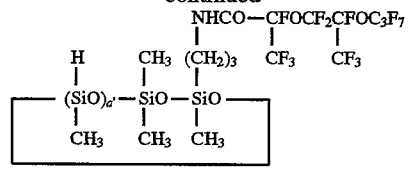

(wherein a' is 2 or 3)

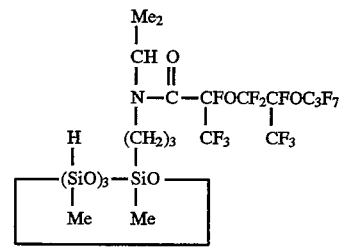

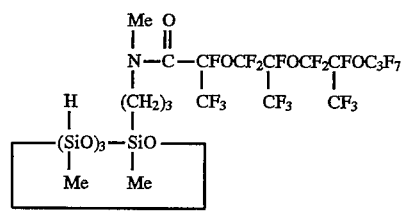

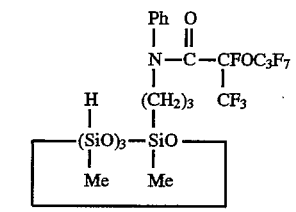

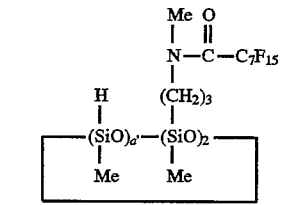

(wherein a' is 2 or 3)

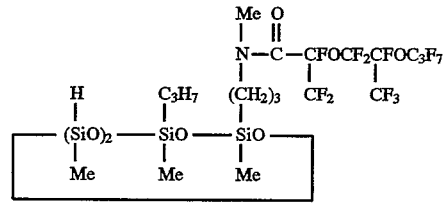

Production of Organosilicon Compound

The organosilicon compound of the present invention can be produced by, for example, subjecting a cyclic hydrosiloxane represented by the following general formula (2):

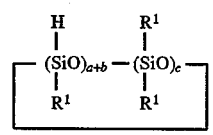

(2)

wherein $R^1$, a, b and c are as defined above; and a fluorine-containing amide compound containing an unsaturated group, represented by the following general formula (3):

$$Rf—CO—N(R^3)—(CH_2)_m—CH=CH_2 \quad (3)$$

wherein m is an integer of 0 to 4, and Rf and $R^3$ are as defined above;

to partial addition reaction in the presence of a catalyst.

Usually the above reaction may be carried out at a temperature of from 50° to 150° C., in particular, from 60° to 120° C. As the catalyst, platinum family metal catalysts well known as catalysts for hydrosilylation may be used, which are exemplified by chloroplatinic acid; alcohol-modified chloroplatinic acid (see U.S. Pat. No. 3,220,972); complexes of chloroplatinic acid with olefins (see U.S. Pat. No. 3,159,601, No. 3,159,662 and No. 3,775,452); platinum black or palladium supported on a carrier such as alumina, silica or carbon; rhodium-olefin complexes; and chlorotris (triphenylphosphine)rhodium (Wilkinson's catalyst). Of these, complex type catalysts may preferably be used in the form of solutions prepared by dissolving them in solvents such as alcohols, ketones or ethers.

The value of b in the above general formula (1) depends on the addition reaction weight of the above fluorine-containing amide compound. Hence, the amount of the fluorine-containing amide compound used in the reaction is set in accordance with the content of SiH group in the cyclic hydrosiloxane to be reacted, so as to obtain the value of b as defined in the general formula (1). The catalyst may be used in an amount of so-called a catalytic weight, e.g., of from 1 to 1,000 ppm, and preferably from 10 to 500 ppm, in terms of platinum family metal per cyclic hydrosiloxane.

The organosilicon compound of the present invention thus obtained is, as previously stated, useful as a crosslinking agent for addition-curable silicone rubber compositions. For example, the organosilicon compound of the present invention may be mixed in such an amount that the content of SiH group comes to be from 0.5 to 5 mols, in particular, from 0.8 to 3 moles, per mole of the alkenyl group, and a curing catalyst, a filler and so forth may be further mixed to form a curable silicone rubber composition, which then can be used in various purposes. Especially when a polymer into which fluorine groups have been introduced is used as the base polymer, it can be especially expected to improve the adhesion of cured products to various substrates.

EXAMPLES

Example 1

Into a 1 liter four-necked flask provided with a stirrer, a thermometer, a reflux condenser and a dropping funnel, 12 g of 1,3,5,7-tetramethylcyclotetrasiloxane and 0.05 g of a toluene solution of a complex of chloroplatinic acid with 1,3-divinyl-1,1,3,3-tetramethyldisiloxane were charged, followed by heating to 80° C. Into this flask, 26.8 g of a fluorine-containing allylamide represented by the following formula:

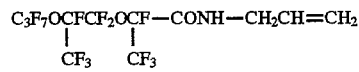

was dropwise added over a period of 1 hour. The reaction was further carried out for 1 hour at 80° C., and thereafter the reaction mixture was distilled under reduced pressure to obtain 14.4 g of a fraction (yield: 37.2%) having a boiling point of 136° to 138 ° C./mmHg and a refractive index of 1.3586 (25 ° C.). On this fraction, $^1$H-NMR, $^{19}$F-NMR and IR absorption were measured and elementary analysis was carried out to obtain the results as shown below.

$^1$H-NMR (TMS standard):

δ: 0.47 ppm (s, Si—CH$_3$, 12H)
δ: 0.86 ppm (m, Si—CH$_2$, 2H)
δ: 1.93 ppm (m, C—CH$_2$—C, 2H)
δ: 3.56 ppm (q, N—CH$_2$, 2H)
δ: 4.90 ppm (s, Si—H, 2H)
δ: 6.70 ppm (s, N—H, 1H)

$^{19}$F-NMR (CF$_3$COOH standard):

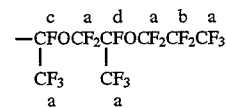

φ: −3.3 to −6.1 ppm (a, 13F)
φ: −52.39 ppm (b, 2F)
φ: −54.78 ppm (c, 1F)
φ: −67.43 ppm (d, 1F)

IR: As shown by a chart in FIG. 1.

$^vN—H$ : 3,330 cm$^{-1}$
$^vSi—H$ : 2,170 cm$^{-1}$
$^vC=O$ : 1,705 cm$^{-1}$
$^δN—H$ : 1,545 cm$^{-1}$

Elementary analysis:

|  | C | H | O | Si |
|---|---|---|---|---|
| Found:(%) | 24.56 | 2.66 | 14.61 | 14.56 |
| Calculated*:(%) | 24.78 | 2.86 | 14.44 | 14.48 |

(*as $C_{16}H_{22}O_7Si_4F_{17}N_1$)

From the above results, the fraction obtained was determined to be an organosilicon compound represented by the following formula:

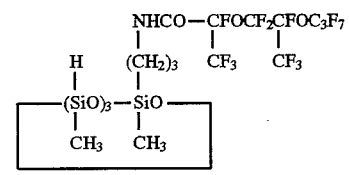

Example 2

Into a 1 liter four-necked flask provided with a stirrer, a thermometer, a reflux condenser and a dropping funnel, 160 g of 1,3,5,7-tetramethylcyclotetrasiloxane and 0.75 g of a toluene solution of a complex of chloroplatinic acid with 1,3-divinyl-1,1,3,3-tetramethyldisiloxane were charged, followed by heating to 80° C. Into this flask, 155.2 g of a fluorine-containing allylamide represented by the following formula:

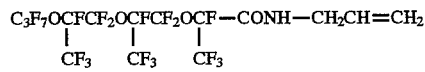

was dropwise added over a period of 1 hour. The reaction was further carried out for 1 hour at 80° C., and thereafter the reaction mixture was distilled under reduced pressure to obtain 120.3 g of a fraction (yield: 57.8%) having a boiling point of 145° to 147° C./mmHg and a refractive index of 1.3508 (25° C.). On this fraction, $^1$H-NMR, $^{19}$F-NMR and IR absorption were measured and elementary analysis was carried out to obtain the results as shown below.

$^1$H-NMR (TMS standard):

δ: 0.43 ppm (s, Si—CH$_3$, 12H)
δ: 0.81 ppm (m, Si—CH$_2$, 2H)
δ: 1.87 ppm (m, C—CH$_2$—C, 2H)
δ: 3.54 ppm (q, N—CH$_2$, 2H)
δ: 4.91 ppm (s, Si—H, 2H)
δ: 6.47 ppm (s, N—H, 1H)

$^{19}$F-NMR (CF$_3$COOH standard):

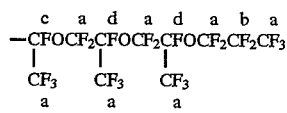

φ: −3.3 to −5.6 ppm (a, 18F)
φ: −52.49 ppm (b, 2F)
φ: −54.39 ppm (c, 1F)
φ: −67.38 ppm (d, 2F)

Figure 2:
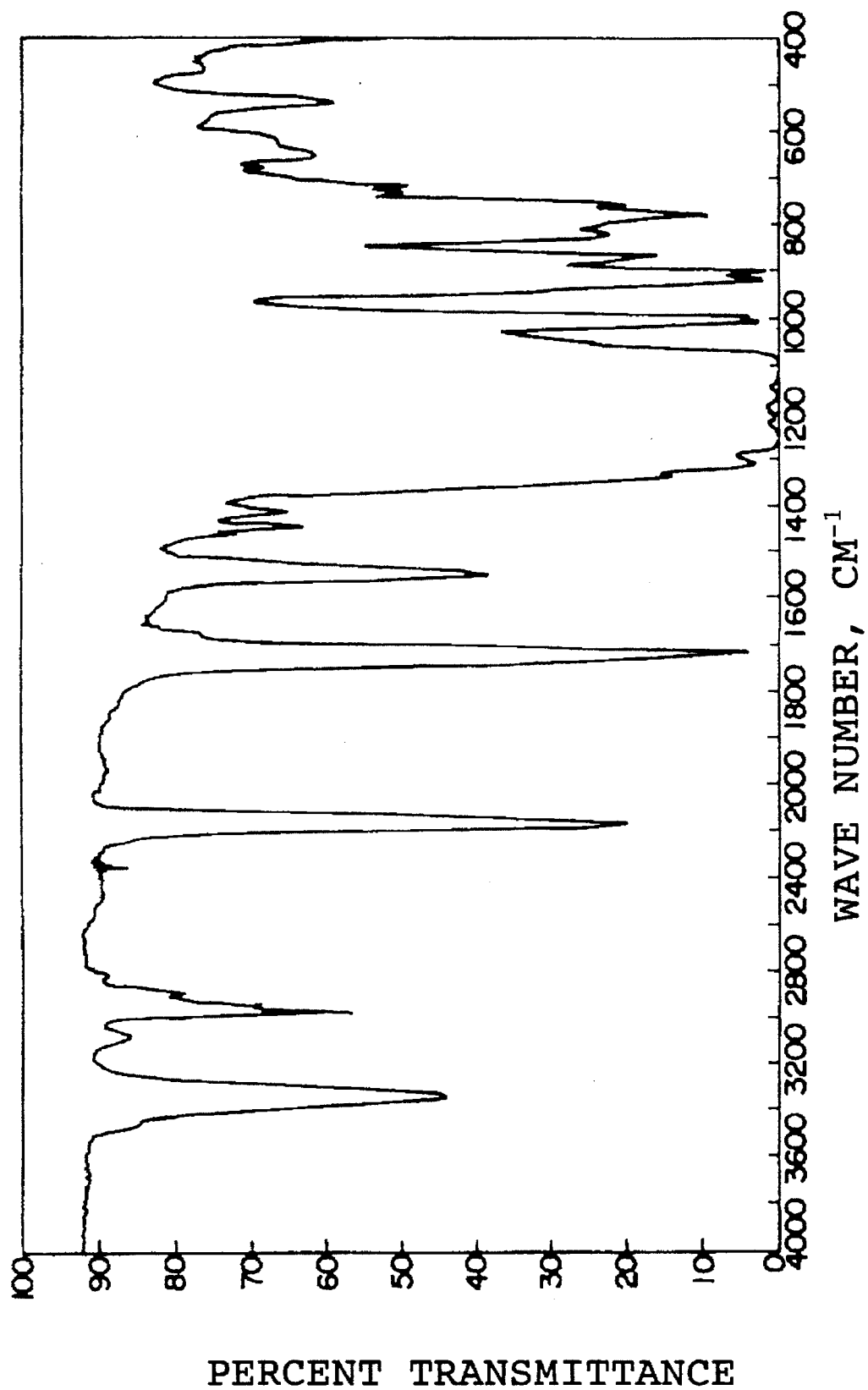
FIG. 2 is an IR chart of a compound synthesized in Example 2.

IR: As shown by a chart in FIG. 2.
$^\nu$N—H : 3,330 cm$^{-1}$
$^\nu$Si—H : 2,170 cm$^{-1}$
$^\nu$C=O : 1,700 cm$^{-1}$
$^\delta$N—H : 1,540 cm$^{-1}$ Elementary analysis:

|  | C | H | O | Si |
|---|---|---|---|---|
| Found:(%) | 24.32 | 2.31 | 13.61 | 11.88 |
| Calculated*:(%) | 24.23 | 2.35 | 13.59 | 11.93 |

(*as C$_{19}$H$_{22}$O$_8$Si$_4$F$_{23}$N$_1$)

From the above results, the fraction obtained was determined to be an organosilicon compound represented by the following formula:

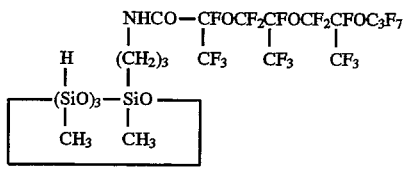

Example 3

Into a 1 liter four-necked flask provided with a stirrer, a thermometer, a reflux condenser and a dropping funnel, 120 g of 1,3,5,7-tetramethylcyclotetrasiloxane and 0.5 g of a toluene solution of a complex of chloroplatinic acid with 1,3-divinyl-1,1,3,3-tetramethyldisiloxane were charged, followed by heating to 80° C. Into this flask, 184.5 g of a fluorine-containing allylamide represented by the following formula:

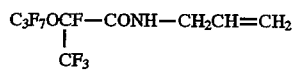

was dropwise added over a period of 1 hour. The reaction was further carried out for 1 hour at 80° C., and thereafter the reaction mixture was distilled under reduced pressure to obtain 76.2 g of fraction A (yield: 25.0%) having a boiling point of 130° to 132° C./mmHg and a refractive index of 1.3722 (25° C.) and 5.9 g of fraction B (yield: 1.2%) having a boiling point of 190° to 192° C./mmHg and a refractive index of 1.3694 (25° C.).

On these fractions, $^1$H-NMR, $^{19}$F-NMR and IR absorption were measured and elementary analyses were carried out to obtain the results as shown below.

Re Fraction A $^1$H-NMR (TMS standard):

δ: 0.34 ppm (s, Si—CH$_3$, 12H)
δ: 0.77 ppm (m, Si—CH$_2$, 2H)
δ: 1.81 ppm (m, C—CH$_2$—C, 2H)
δ: 3.47 ppm (q, N—CH$_2$, 2H)
δ: 4.83 ppm (s, Si—H, 2H)
δ: 7.04 ppm (s, N—N—H, 1H)

$^{19}$F-NMR (CF$_3$COOH standard):

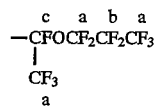

φ: −4.8 to −6.7 ppm (a, 8F)
φ: −52.58 ppm (b, 2F)
φ: −54.93 ppm (c, 1F)

Figure 3:
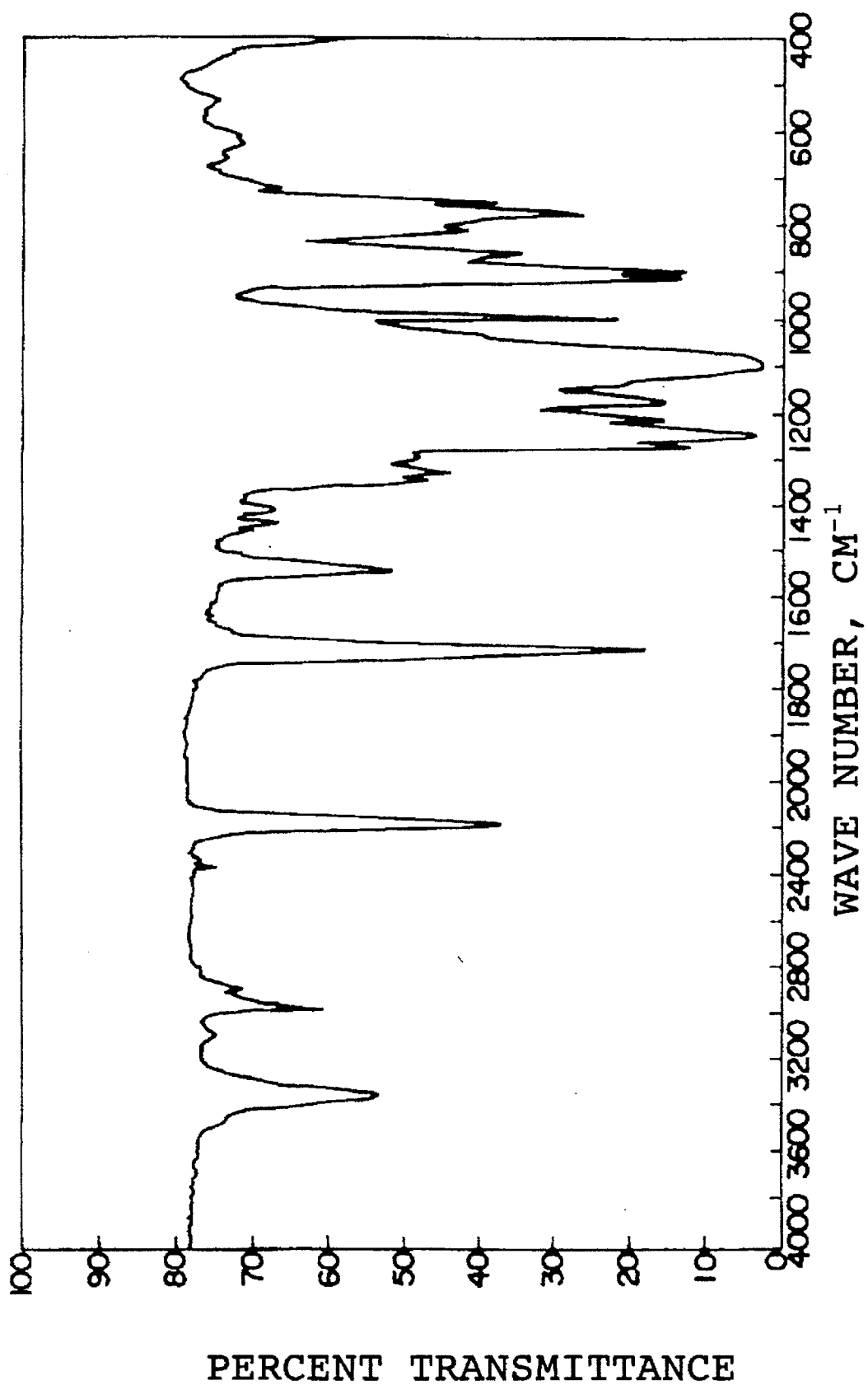
FIG. 3 is an IR chart of a compound of fraction A obtained in Example 3.

IR: As shown by a chart in FIG. 3.
$^\nu$N—H : 3,330 cm$^{-1}$
$^\nu$Si—H : 2,170 cm$^{-1}$
$^\nu$C=O : 1,700 cm$^{-1}$
$^\delta$N—H : 1,540 cm$^{-1}$ Elementary analysis:

|  | C | H | O | Si |
|---|---|---|---|---|
| Found:(%) | 25.57 | 3.66 | 15.84 | 18.52 |
| Calculated*:(%) | 24.61 | 3.64 | 15.75 | 18.43 |

(*as C$_{13}$H$_{22}$O$_6$Si$_4$F$_{11}$N$_1$)

From the above results, the fraction A obtained was determined to be an organosilicon compound represented by the following formula:

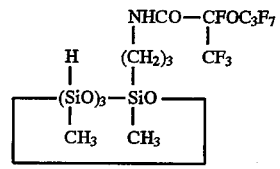

Re Fraction B $^1$H-NMR (TMS standard):

δ: 0.33 ppm (s, Si—CH$_3$, 12H)
δ: 0.77 ppm (m, Si—CH$_2$, 4H)
δ: 1.86 ppm (m, C—CH$_2$—C, 4H)
δ: 3.49 ppm (q, N—CH$_2$, 4H)
δ: 4.87 ppm (s, Si—H, 2H)
δ: 7.70 ppm (s, N—H, 2H)

$^{19}$F-NMR (CF$_3$COOH standard):

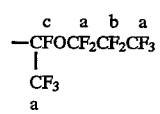

φ: −4.3 to −6.4 ppm (a, 16F)
φ: −52.19 ppm (b, 4F)

φ: −54.64 ppm (c, 2F)

Figure 4:
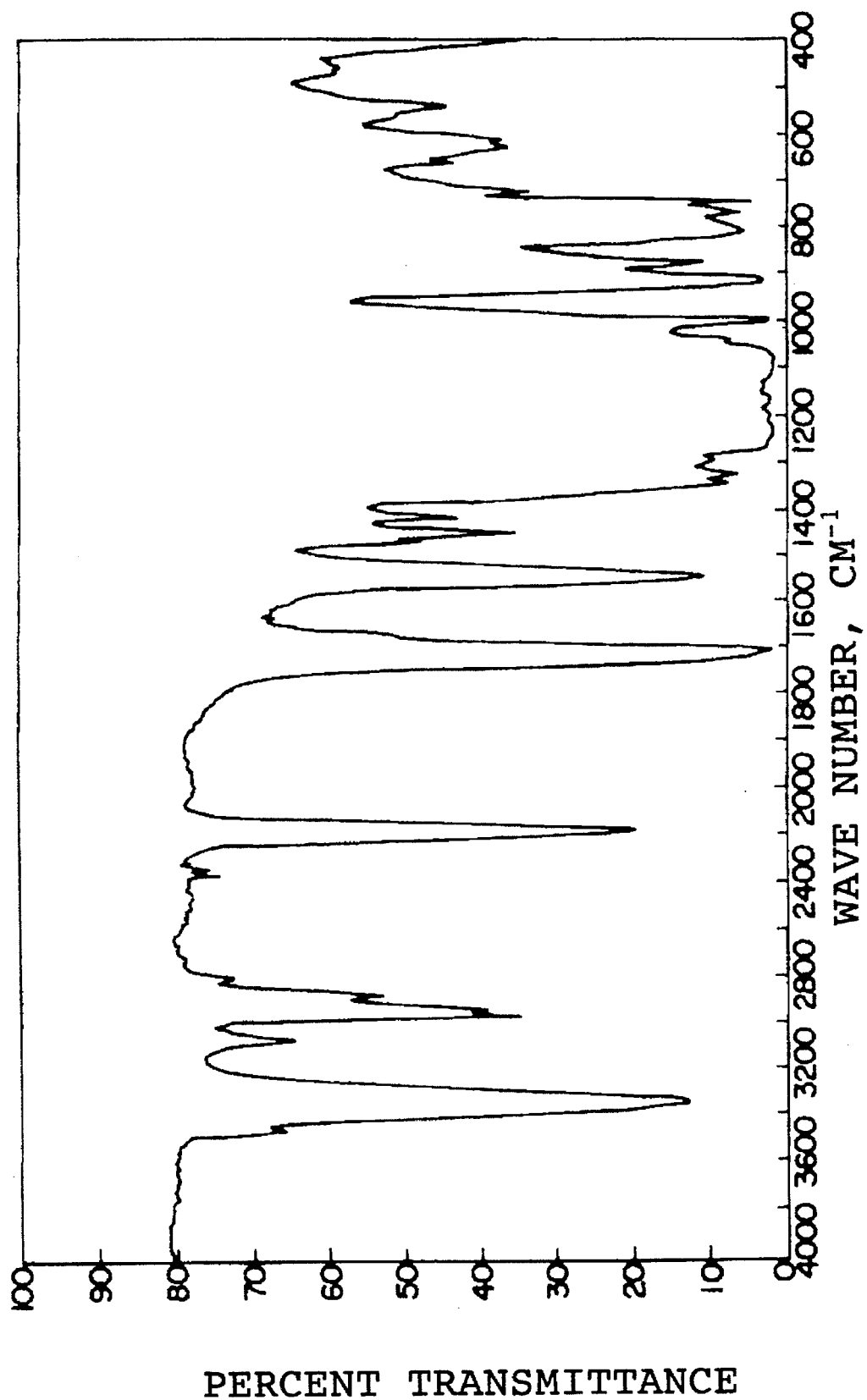
FIG. 4 is an IR chart of a compound of fraction B obtained in Example 4.

IR: As shown by a chart in FIG. 4

$^{v}$N—H : 3,330 cm$^{-1}$ $^{v}$Si—H : 2,170 cm$^{-1}$ $^{v}$C=O : 1,700 cm$^{-1}$ $^{δ}$N—H : 1,540 cm$^{-1}$

Elementary analysis:

|  | C | H | O | Si |
|---|---|---|---|---|
| Found:(%) | 26.89 | 2.76 | 13.15 | 11.53 |
| Calculated*:(%) | 27.00 | 2.88 | 13.08 | 11.48 |

(*as $C_{22}H_{28}O_8Si_4F_{22}N_2$)

From the above results, the fraction B obtained was determined to be an organosilicon compound represented by the following formula:

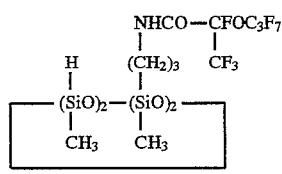

Example 4

Into a 1 liter four-necked flask provided with a stirrer, a thermometer, a reflux condenser and a dropping funnel, 282 g of 1,3,5,7-tetramethyl-1-propylcyclotetrasiloxane and 2.0 g of a toluene solution of a complex of chloroplatinic acid with 1,3-divinyl-1,1,3,3-tetramethyldisiloxane were charged, followed by heating to 80° C. Into this flask, 178.3 g of a fluorine-containing allylamide represented by the following formula:

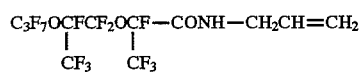

was dropwise added over a period of 1 hour. The reaction was further carried out for 1 hour at 80° C., and thereafter the reaction mixture was distilled under reduced pressure to obtain 128.6 g of a fraction (yield: 47.2%) having a boiling point of 140° to 142° C./mmHg and a refractive index of 1.3666 (25° C.). on this fraction, $^1$H-NMR, $^{19}$F-NMR and IR absorption were measured and elementary analysis was carried out to obtain the results as shown below.

$^1$H-NMR (TMS standard):

δ: 0.47 ppm (s, Si—CH$_3$, 12H)

δ: 0.86 ppm (m, Si—CH$_2$, 2H)

δ: 1.93 ppm (m, C—CH$_2$—C, 2H)

δ: 3.56 ppm (q, N—CH$_2$, 2H)

δ: 4.90 ppm (s, Si—H, 2H)

δ: 6.70 ppm (s, N—H, 1H)

$^{19}$F-NMR (CF$_3$COOH standard):

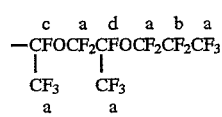

φ: −3.3 to −5.7 ppm (a, 13F)

φ: −52.44 ppm (b, 2F)

φ: −54.44 ppm (c, 1F)

φ: −67.29 ppm (d, 1F)

Figure 5:
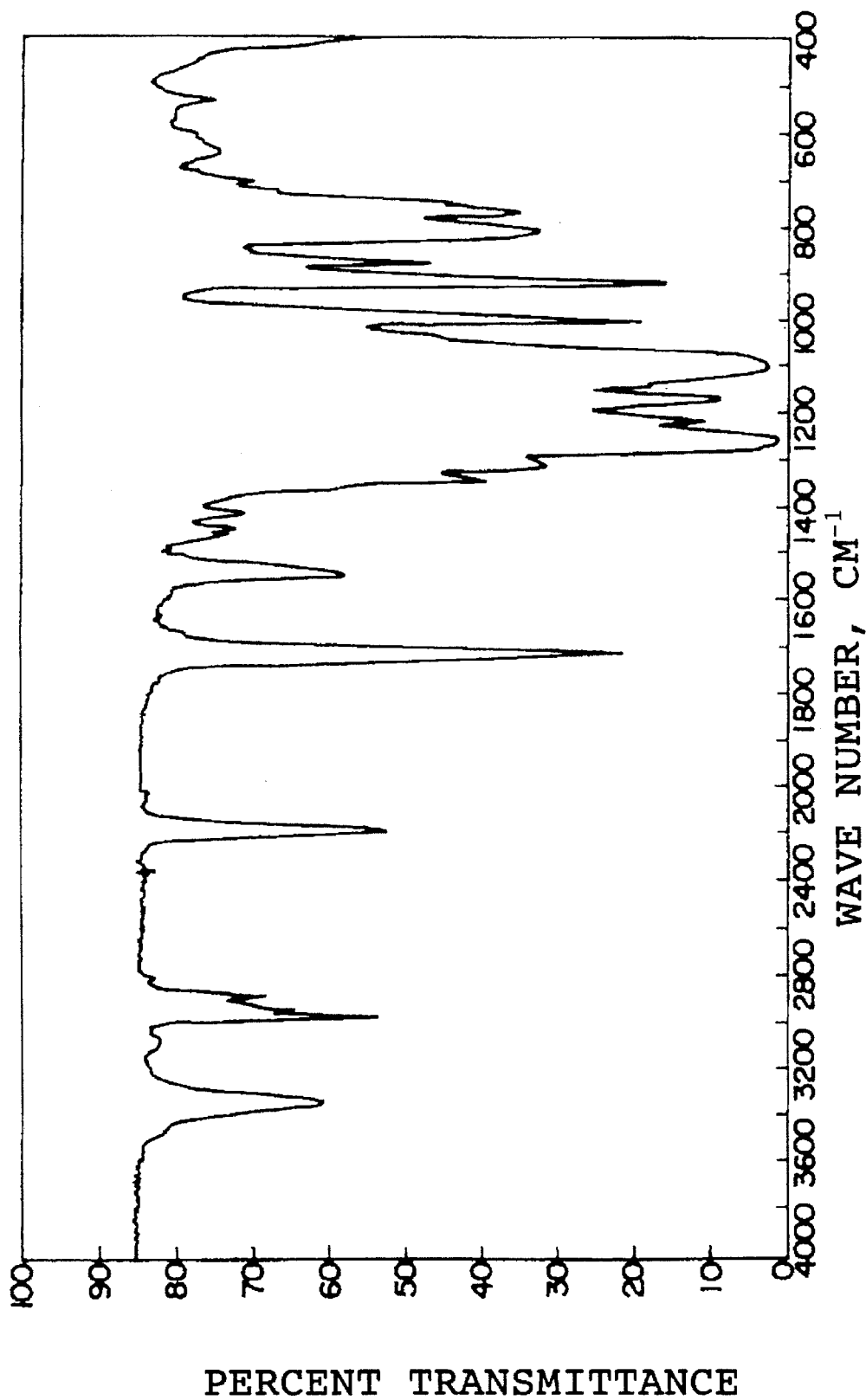
FIG. 5 is an IR chart of a compound synthesized in Example 4.

IR: As shown by a chart in FIG. 5.

$^{v}$N—H : 3,330 cm$^{-1}$ $^{v}$Si—H : 2,170 cm$^{-1}$ $^{v}$C=O : 1,700 cm$^{-1}$ $^{δ}$N—H : 1,540 cm$^{-1}$

Elementary analysis:

|  | C | H | O | Si |
|---|---|---|---|---|
| Found:(%) | 27.99 | 3.56 | 13.88 | 13.56 |
| Calculated*:(%) | 24.91 | 3.45 | 13.74 | 13.74 |

(*as $C_{19}H_{25}O_7Si_4F_{17}N_1$)

From the above results, the fraction obtained was determined to be an organosilicon compound represented by the following formula:

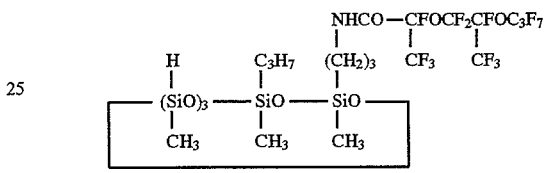

Example 5

Into a 1 liter four-necked flask provided with a stirrer, a thermometer, a reflux condenser and a dropping funnel, 86.4 g of 1,3,5,7-tetramethylcyclotetrasiloxane and 0.35 g of a toluene solution of a complex of chloroplatinic acid with 1,3-divinyl-1,1,3,3-tetramethyldisiloxane were charged, followed by heating to 80° C. Into this flask, 69.2 g of a fluorine-containing allylamide represented by the following formula:

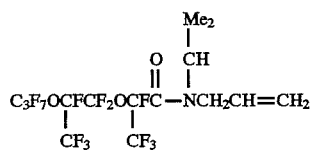

was dropwise added over a period of 1 hour. The reaction was further carried out for 1 hour at 80° C., and thereafter the reaction mixture was distilled under reduced pressure to obtain 26.5 g of a fraction (yield: 27.0%) having a boiling point of 138° to 140° C./2 mmHg and a refractive index of 1.3650 (25° C.). On this fraction, $^1$H-NMR, $^{19}$F-NMR and IR absorption were measured and elementary analysis was carried out to obtain the results as shown below.

$^1$H-NMR (TMS standard):

δ: 0.21 ppm (s, Si—CH$_3$, 12H)

δ: 0.56 ppm (m, Si—CH$_2$, 2H)

δ: 1.26 ppm (d, C—CH$_3$, 6H)

δ: 1.65 ppm (m, C—CH$_2$—C, 2H)

δ: 3.20 ppm (q, N—CH$_2$, 2H)

δ: 4.25 ppm (q, N—CH$_2$, 1H)

δ: 4.66 ppm (s, Si—H, 3H)

Figure 6:
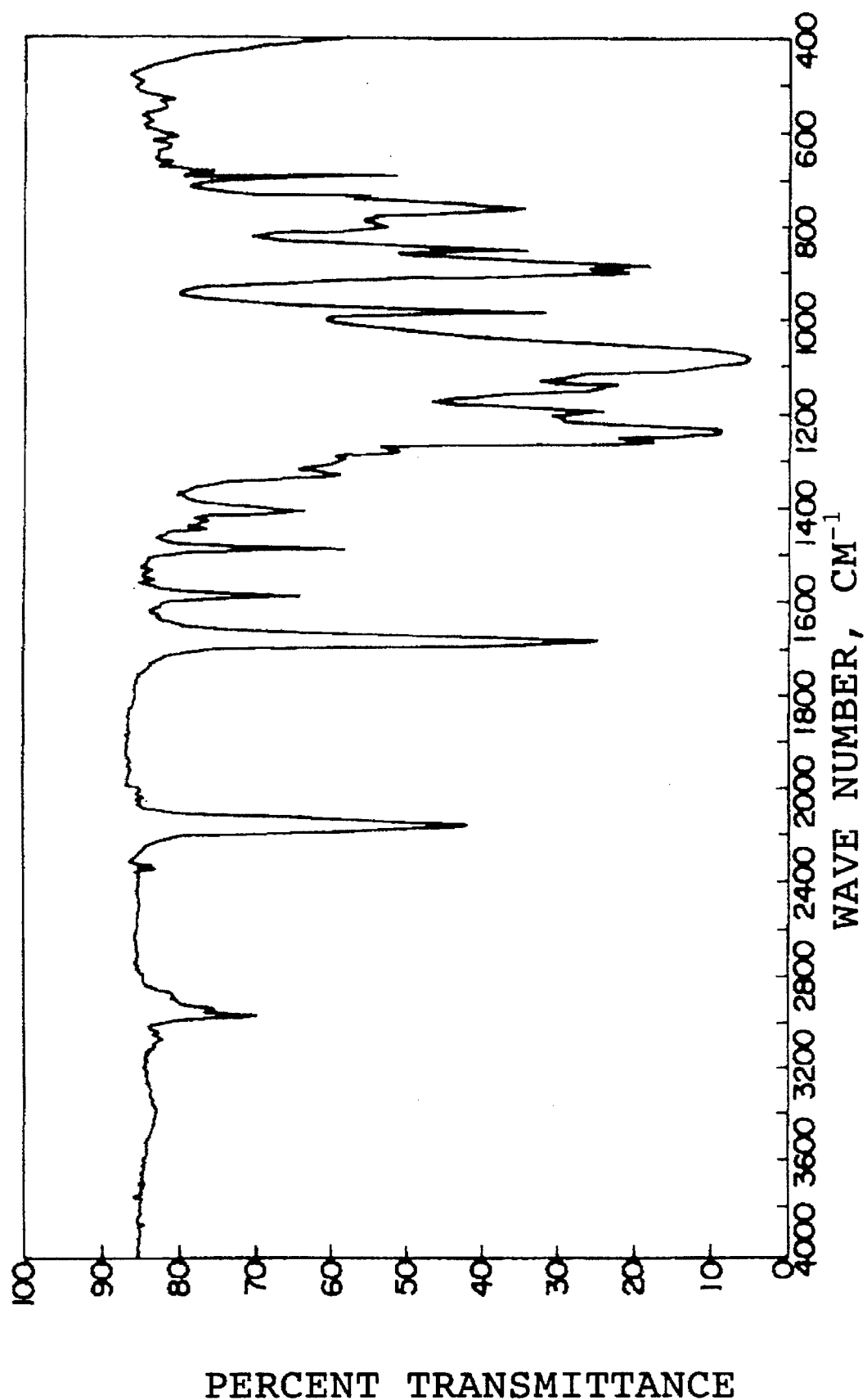
FIG. 6 is an IR chart of a compound synthesized in Example 5.

$^{19}$F-NMR (CF$_3$COOH standard):

$$\begin{array}{c} \text{b\phantom{x}a\phantom{x}d\phantom{x}a\phantom{x}c\phantom{x}a} \\ -\text{CFOCF}_2\text{CFOCF}_2\text{CF}_2\text{CF}_3 \\ |\phantom{xxxxxx}| \\ \text{CF}_3\phantom{xxx}\text{CF}_3 \\ \text{a}\phantom{xxxx}\text{a} \end{array}$$

φ: −2.8 to −6.1 ppm (a, 13F)
φ: −47.65 ppm (b, 1F)
φ: −52.58 ppm (c, 2F)
φ: −67.82 ppm (d, 1F)
IR: As shown by a chart in FIG. 6.
$^v$Si—H : 2,170 cm$^{-1}$
$^v$C=O : 1,675 cm$^{-1}$
Elementary analysis:

|  | C | H | O | Si |
|---|---|---|---|---|
| Found:(%) | 27.91 | 3.45 | 13.70 | 13.74 |
| Calculated*:(%) | 24.07 | 3.30 | 13.85 | 13.72 |

(*as C$_{19}$H$_{28}$O$_7$Si$_4$F$_{17}$N$_1$)

From the above results, the compound obtained was determined to be an organosilicon compound represented by the following formula:

$$\begin{array}{c} \phantom{xxxxxx}\text{Me}_2 \\ \phantom{xxxxxx}| \\ \phantom{xxxxxx}\text{CH}\phantom{xx}\text{O} \\ \phantom{xxxxxx}|\phantom{xxx}|| \\ \phantom{xxxxxx}\text{N}-\text{C}-\text{CFOCF}_2\text{CFOC}_3\text{F}_7 \\ \text{H}\phantom{xxx}|\phantom{xxxxxxx}|\phantom{xxxx}| \\ |\phantom{xxx}(\text{CH}_2)_3\phantom{xx}\text{CF}_3\phantom{xx}\text{CF}_3 \\ \boxed{-(\text{SiO})_3\text{—SiO—}} \\ |\phantom{xxxxxxxxx}| \\ \text{Me}\phantom{xxxxxx}\text{Me} \end{array}$$

Example 6

Into a 1 liter four-necked flask provided with a stirrer, a thermometer, a reflux condenser and a dropping funnel, 36 g of 1,3,5,7-tetramethylcyclotetrasiloxane and 0.1 g of a toluene solution of a complex of chloroplatinic acid with 1,3-divinyl-1,1,3,3-tetramethyldisiloxane were charged, followed by heating to 80° C. Into this flask, 21.6 g of a fluorine-containing allylamide represented by the following formula:

$$\begin{array}{c} \text{O}\phantom{xx}\text{Ph} \\ ||\phantom{xx}| \\ \text{C}_3\text{F}_7\text{OCFC}-\text{N}-\text{CH}_2\text{CH}=\text{CH}_2 \\ | \\ \text{CF}_3 \end{array}$$

was dropwise added over a period of 1 hour. The reaction was further carried out for 1 hour at 80° C., and thereafter the reaction mixture was distilled under reduced pressure to obtain 15.5 g of a fraction (yield: 46.1%) having a boiling point of 145° to 147° C./1 mmHg and a refractive index of 1.4032 (25° C.). On this fraction, $^1$H-NMR, $^{19}$F-NMR and IR absorption were measured and elementary analysis was carried out to obtain the results as shown below.

$^1$H-NMR (TMS standard):
δ: 0.17 ppm (m, Si—CH$_3$, 12H)
δ: 0.56 ppm (m, Si—CH$_2$, 2H)
δ: 1.67 ppm (m, C—CH2—C, 2H)
δ: 3.67 ppm (t, N—CH$_2$, 2H)
δ: 4.64 ppm (s, Si—H, 3H)
δ: 6.9 to 7.5 ppm (s, arom, 1H)

Figure 7:
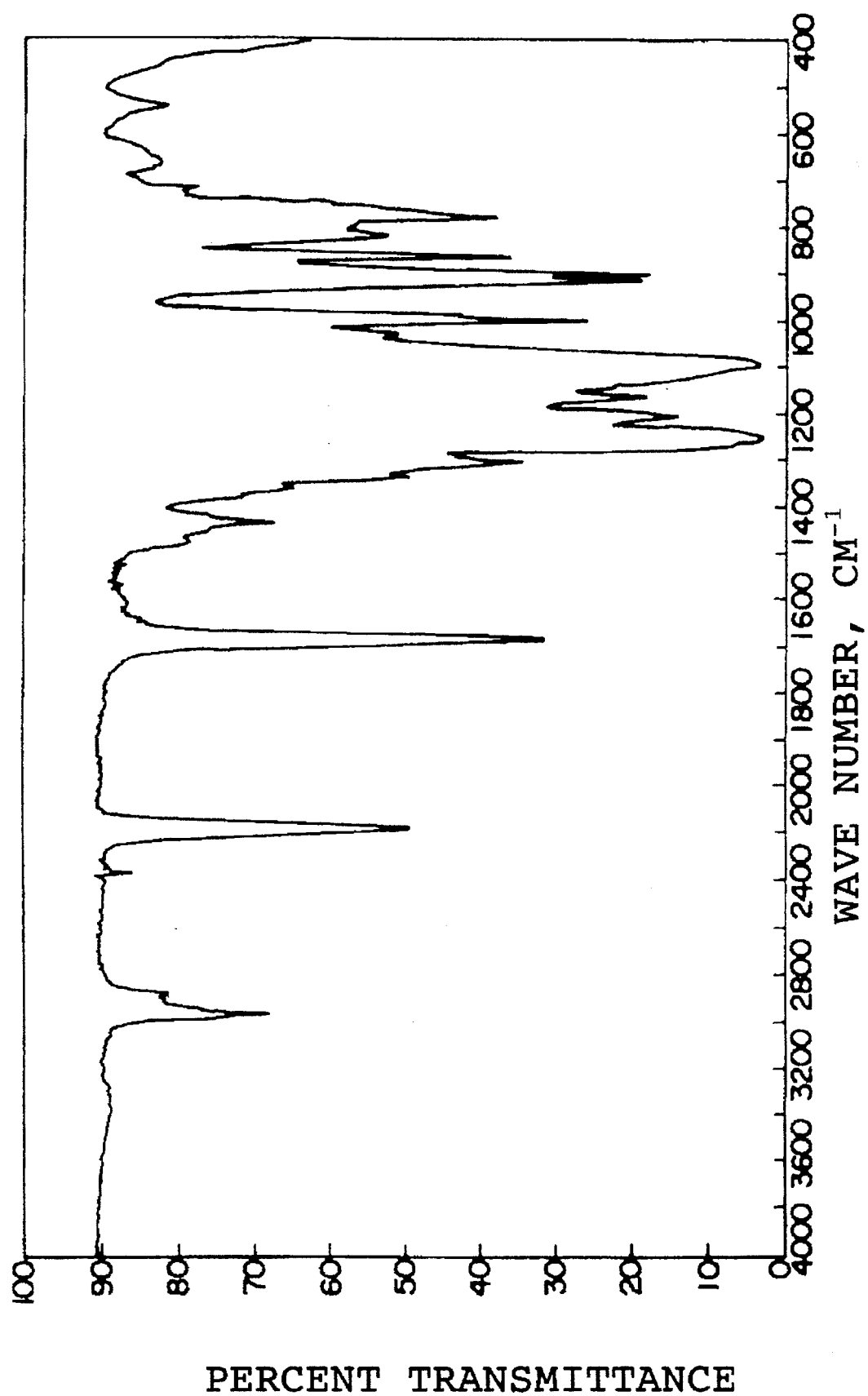
FIG. 7 is an IR chart of a compound synthesized in Example 6.

$^{19}$F-NMR (CF$_3$COOH standard):

$$\begin{array}{c} \text{b\phantom{x}a\phantom{x}c\phantom{x}a} \\ -\text{CFOCF}_2\text{CF}_2\text{CF}_3 \\ | \\ \text{CF}_3 \\ \text{a} \end{array}$$

φ: −3.5 to −8.2 ppm (a, 8F)
φ: −45.41 ppm (b, 1F)
φ: −52.68 ppm (c, 2F)
IR: As shown by a chart in FIG. 7.
$^v$Si—H : 2,170 cm$^{-1}$
$^v$C=O : 1,685 cm$^{-1}$
arom : 1,595 cm$^{-1}$
arom : 1,495 cm$^{-1}$
Elementary analysis:

|  | C | H | O | Si |
|---|---|---|---|---|
| Found:(%) | 32.09 | 3.89 | 14.25 | 16.67 |
| Calculated*:(%) | 32.13 | 3.71 | 14.33 | 16.83 |

(*as C$_{19}$H$_{26}$O$_6$Si$_4$F$_{11}$N$_1$)

From the above results, the compound obtained was determined to be an organosilicon compound represented by the following formula:

$$\begin{array}{c} \phantom{xxxxxx}\text{Ph}\phantom{xx}\text{O} \\ \phantom{xxxxxx}|\phantom{xxx}|| \\ \phantom{xxxxxx}\text{N}-\text{C}-\text{CFOC}_3\text{F}_7 \\ \text{H}\phantom{xxx}|\phantom{xxxxxxx}| \\ |\phantom{xxx}(\text{CH}_2)_3\phantom{xx}\text{CF}_3 \\ \boxed{-(\text{SiO})_3\text{—SiO—}} \\ |\phantom{xxxxxxxxx}| \\ \text{CH}_3\phantom{xxxx}\text{CH}_3 \end{array}$$

We claim:

1. An organosilicon compound represented by the following general formula (1):

$$\begin{array}{c} \phantom{xxxxxxx}\text{R}^3 \\ \phantom{xxxxxxx}| \\ \phantom{xxxxxxx}\text{N}-\text{CO}-\text{Rf} \\ \text{H}\phantom{xxx}|\phantom{xxxxxxxxx} \\ |\phantom{xxx}\text{R}^2\phantom{xxxxxx}\text{R}^1 \\ |\phantom{xxxxxxxx}|\phantom{xxxxxx}| \\ \boxed{-(\text{SiO})_a-(\text{SiO})_b-(\text{SiO})_c-} \\ |\phantom{xxxxxxxx}|\phantom{xxxxxx}| \\ \text{R}^1\phantom{xxxxx}\text{R}^1\phantom{xxxxx}\text{R}^1 \end{array} \quad (1)$$

wherein:

Rf represents a perfluoroalkyl ether group of the formula $$\begin{array}{c} -\text{CF}-(\text{OCF}_2\text{CF})_n-\text{F} \\ |\phantom{xxxxxxx}| \\ \text{CF}_3\phantom{xxxx}\text{CF}_3 \end{array}$$

wherein n is an integer of 1 to 5;
R$^1$ may be the same or different and each represent a monovalent hydrocarbon group;
R$^2$ represents an alkylene group;
R$^3$ represents a hydrogen atom or a monovalent hydrocarbon group; and
a is an integer of 1 to 4, b is an integer of 1 to 3 and c is zero, provided that a, b and c satisfy the relationship of 3 ≦ a+b+c ≦ 6.

2. The organosilicon compound according to claim 1, wherein said Rf in the general formula (1) is a perfluoroalkyl ether group of the indicated formula having 5 to 17 carbon atoms.

3. The organosilicon compound according to claim 1, wherein said $R^1$ in the general formula (1) is a monovalent hydrocarbon group having 1 to 10 carbon atoms, containing no aliphatic unsaturated bond.

4. The organosilicon compound according to claim 3, wherein said $R^1$ is an alkyl group having 1 to 6 carbon atoms.

5. The organosilicon compound according to claim 1, wherein said $R^2$ in the general formula (1) is an alkylene group having 1 to 6 carbon atoms.

6. The organosilicon compound according to claim 1, wherein said $R^3$ in the general formula (1) is a hydrogen atom or a monovalent hydrocarbon group having 1 to 8 carbon atoms.

7. The organosilicon compound according to claim 1, wherein said $R^3$ is selected from the group consisting of a hydrogen atom, an alkyl group having 1 to 6 carbon atoms and a phenyl group.

8. A process for producing an organosilicon compound represented by the following general formula (1):

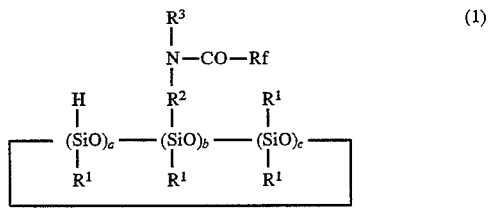

wherein:

Rf represents a perfluoroalkyl ether group of the formula

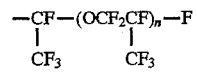

wherein n is an integer of 1 to 5;

$R^1$ may be the same or different and each represent a monovalent hydrocarbon group;

$R^2$ represents an alkylene group;

$R^3$ represents a hydrogen atom or a monovalent hydrocarbon group; and a is an integer of 1 to 4, b is an integer of 1 to 3 and c is zero, provided that a, b and c satisfy the relationship of $3 \leq a+b+c \leq 6$;

said process comprising the step of subjecting a cyclic hydrosiloxane represented by the following general formula (2):

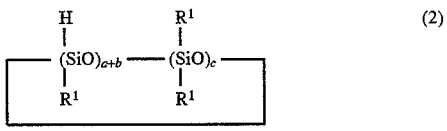

wherein $R^1$, a, b and c are as defined above; and a fluorine-containing amide compound containing an unsaturated group, represented by the following general formula (3):

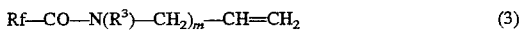

wherein m is an integer of 0 to 4, and Rf and $R^3$ are as defined above;

to partial addition reaction in the presence of a catalyst.

* * * * *